United States Patent [19]

Hofmeister et al.

[11] 4,371,529
[45] Feb. 1, 1983

[54] 11-METHYLENE-Δ¹⁵-STEROIDS, THEIR PREPARATION AND USE IN PHARMACEUTICALS

[75] Inventors: Helmut Hofmeister; Karl Petzoldt; Klaus Annen; Henry Laurent; Rudolf Wiechert; Hermann Steinbeck, all of Berlin, Fed. Rep. of Germany

[73] Assignee: Schering, Aktiengesellschaft, Berlin and Bergkamen, Fed. Rep. of Germany

[21] Appl. No.: 318,906

[22] Filed: Nov. 6, 1981

[30] Foreign Application Priority Data

Nov. 7, 1980 [DE] Fed. Rep. of Germany ....... 3042529

[51] Int. Cl.³ .............................................. A61K 31/56
[52] U.S. Cl. ................................ 424/243; 260/397.45
[58] Field of Search ............... 260/397.4, 397.45; 424/243

[56] References Cited

U.S. PATENT DOCUMENTS 3,475,463 10/1969 Phillips .......................... 260/397.4
3,927,046 12/1975 van den Broek ............... 260/397.4
4,081,537 3/1978 Hofmeister et al. ............. 260/397.4
4,277,468 7/1981 Hofmeister et al. ........... 260/397.45

*Primary Examiner*—Elbert L. Roberts
*Attorney, Agent, or Firm*—Millen & White

[57] ABSTRACT

11-Methylene-Δ¹⁵-steroids of Formula I

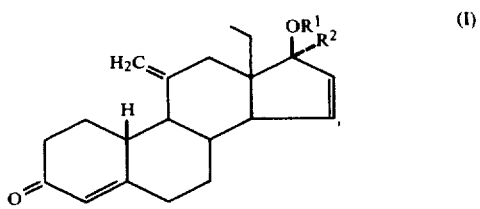

wherein
$R^1$ is hydrogen or acyl and
$R^2$ is ethynyl, chloroethynyl or propynyl,
are distinguished by a strong progestational activity and exhibit only a very low androgenic side effect.

14 Claims, No Drawings

11-METHYLENE-Δ¹⁵-STEROIDS, THEIR PREPARATION AND USE IN PHARMACEUTICALS

BACKGROUND OF THE INVENTION

The present invention relates to 11-methylene-Δ¹⁵-steroids, a process for their preparation, and pharmaceutical preparations containing them.

It is well-known that 11-methylene steroids possess valuable biological properties. In DOS [German Unexamined Laid-Open Application] No. 2,361,120, for example, 11-methylene-17α-ethynyl-18-methyl-4-estrenes are disclosed which exhibit a strong progestational effect. However, such compounds have disadvantageous androgenic side effects.

SUMMARY OF THE INVENTION

Accordingly, it is an object of this invention to provide compounds having valuable pharmacological activity and which overcome prior art disadvantages.

Upon further study of the specification and appended claims, further objects and advantages of this invention will become apparent to those skilled in the art.

These objects have been attained by providing 11-Methylene-Δ¹⁵-steroids of Formula I

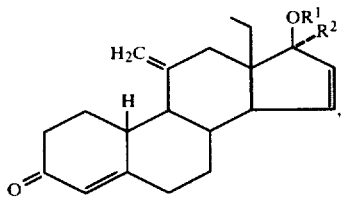

wherein
$R^1$ is hydrogen or acyl and
$R^2$ is ethynyl, chloroethynyl or propynyl.

DETAILED DISCUSSION

Suitable acyl groups $R^1$ are conventional and are derived from acids usually employed for esterification reactions in steroid chemistry. Its precise nature is not critical. Preferred acids are organic hydrocarbon carboxylic acids of up to 15 carbon atoms, especially lower and intermediate aliphatic carboxylic acids of up to 7 carbon atoms, e.g., preferred acyl groups are $C_{1-7}$ alkanoyl groups. These acids can be unsaturated, branched, polybasic, or substituted in conventional fashion, e.g. by hydroxy, acyloxy, alkoxy, oxo, or amino groups, or halogen atoms. Likewise suitable are cycloaliphatic, aromatic, mixed aromatic-aliphatic, and heterocyclic acids which can also be substituted in the usual way. All such acids are equivalents for this invention.

Examples in this connection include the following carboxylic acids: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, β-cyclopentylpropionic acid, cyclohexylacetic acid, cyclohexanecarboxylic acid, phenylacetic acid, phenoxyacetic acid, mono-, di-, and trichloroacetic acids, aminoacetic acid, diethylaminoacetic acid, piperidinoacetic acid, morpholinoacetic acid, lactic acid, O-tridecanoylglycolic acid, succinic acid, adipic acid, benzoic acid, nicotinic acid, isonicotinic acid, furan-2-carboxylic acid and the like.

The novel 11-methylene-Δ¹⁵-steroids of this invention can be produced by introducing the residue $R^2$ into an 18-methyl-11-methylene-4,15-estradien-17-one. For example, they can be prepared by appropriately introducing the residue $R^2$ into a 17-oxo steroid of Formula II

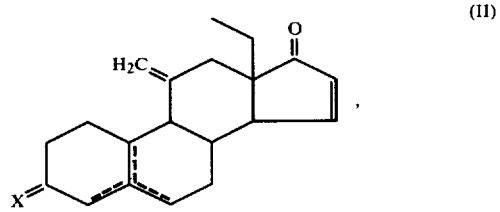

wherein X is an acid-hydrolyzable oxo blocking group and

is a double bond in the 4,5-, 5,6- or 5,10-position, or two double bonds, one emanating from the 3- and one from the 5-position, according to conventional methods, using an agent releasing the residue $R^2$, with the formation of a tertiary carbinol at the 17-C atom; hydrolyzing the 3-oxo blocking group; and, depending on the particular $R^1$ group desired, optionally esterifying the 17-hydroxy group before or after splitting off the oxo blocking group.

The residue $R^2$ can be introduced by following conventional methods, e.g., using an organometallic ethynyl, chloroethynyl, or propynyl compound. Suitable organometallic compounds include, for instance, alkali metal acetylides, such as, for example, potassium acetylide and lithium acetylide, potassium and lithium chloroacetylide, and/or potassium and lithium methylacetylide.

The organometallic compound can also be formed in situ and made to react with the 17-ketone of Formula II. Thus, it is possible, for example, to treat the 17-ketone in a suitable solvent with acetylene and an alkali metal, especially potassium, sodium, or lithium, in the presence of a $C_4$- or $C_5$-alcohol (alkanol) or ammonia or in the form of butyllithium, for example. Lithium chloroacetylide can be obtained from 1,2-dichloroethylene and an ethereal methyllithium solution.

Other suitable organometallic ethynyl compounds include ethynylmagnesium or ethynylzinc halides, especially ethynylmagnesium bromide or iodide.

Suitable solvents include dialkyl ethers, tetrahydrofuran, dioxane, benzene, toluene, etc.

The optional subsequent esterification of the 17-hydroxy group can be accomplished according to methods customarily employed for the esterification of tertiary hydroxy groups in steroid chemistry. One suitable esterification method is, for example, the reaction of the steroids with acid anhydrides or acid chlorides in the presence of alkaline catalysts, e.g. sodium bicarbonate, potassium bicarbonate, potassium carbonate, sodium hydroxide, potassium hydroxide, pyridine, lutidine, collidine, triethylamine, or 4-dimethylaminopyridine.

According to a preferred embodiment, the esterification is conducted in the presence of pyridine and 4-dimethylaminopyridine.

The hydrolysis of the 3-oxo blocking group, which can occur before or after the optional esterification, is also effected using methods known to those skilled in the art. Suitable for the hydrolysis are, for example, mineral acids, e.g. perchloric acid, sulfuric acid, or hydrochloric acid, or organic acids, e.g. oxalic acid. The hydrolysis is preferably conducted in an alcoholic solution or in other polar solvents, for example acetone, at temperatures of about 20° to 100° C.

The oxo blocking group X in Formula II forms, with the double bond(s) present in ring A or B, an arrangement of atoms such that the compound is converted, by acid hydrolysis, into a 4,5-unsaturated 3-oxo steroid. According to a preferred embodiment, the 3-oxo group is blocked by ketal formation.

Suitable ketal residues are derived from alcohols and thioalcohols customarily employed for the blockage of free oxo groups; examples in this connection include: ethylene glycol, 2,2-dimethyl-1,3-propanediol, and ethane-1,2-dithiol. The 3-oxo group, however, can also be partially blocked by enol ether, enol ester, or enamine formation.

It has now been found that the novel 11-methylene-$\Delta^{15}$-steroids of this invention have a progestational efficacy which is stronger than or at least equally as strong as that of the known 11-methylene steroids described in DOS No. 2,361,120, but exhibit an androgenic side effect which is surprisingly low as compared with the conventional 11-methylene steroids.

For example, at a dosage of 1 mg of compound, conventionally administered subcutaneously to castrated male rats, in a conventional pharmaceutical protocol the following results were obtained (see U.S. Pat. No. 3,994,937).

| Compound | Weights (mg) | | |
| --- | --- | --- | --- |
| | Seminal Vesicle | Prostate | Levator ani |
| (1) 17α-Ethynyl-17β-hydroxy-18-methyl-11-methylene-4,15-estradien-3-one | 12 | 25 | 29 |
| (2) 17α-Chloroethynyl-17β-hydroxy-18-methyl-11-methylene-4,15-estradien-3-one | 29 | 28 | 22 |
| (3) 17α-Ethynyl-17β-hydroxy-18-methyl-11-methylene-4-estren-3-one | 43 | 72 | 64 |

(DOS 2,361,120)

It can be seen from the table that, by all three measures, the androgenic side effect of the comparison compound of the closest prior art (3) is much more strongly pronounced than for compounds (1) and (2) of this invention.

The compounds of Formula I can be utilized, for example, in contraceptive preparations as the progestational component in combination with an estrogenically effective hormonal component, e.g. ethynylestradiol, or as the sole active component. However, it is also possible to utilize the compounds in preparations for the treatment of gynecological disturbances such as cycle irregularities in case of inadequate function of the corpus luteum, climacteric complaints, depressive mood, etc.

For use, the novel compounds can be processed into the usual medicines together with the additives, vehicles, and flavor-ameliorating agents customary in galenic pharmacy according to conventional methods. Especially suitable for oral administration are tablets, dragees, capsules, pills, suspensions, or solutions. Especially amenable to parenteral administration are oily solutions, e.g. sesame oil or castor oil solutions, which can optionally furthermore contain a diluent, for example benzyl benzoate or benzyl alcohol. The concentration of the active agent is dependent on the form of administration. Thus, for example, tablets for oral administration preferably contain 0.01–0.5 mg of active ingredient, and solutions for parenteral administration contain, preferably, 1–100 mg of active agent per 1 ml of solution.

The dosage of the medicinal agents of this invention will vary conventionally with the form and purpose of administration. For example, the daily contraceptive dose for oral administration is 0.01–0.5 mg. Dosages in any given case can be conventionally determined, e.g. by observing differential potencies vs. known agents via a conventional protocol such as the Clauberg test.

The administration of the compounds of this invention can be conducted analogously to that of the known progestagen norgestrel (U.S. Pat. No. 3,959,322) or lynestrenol (U.S. Pat. No. 2,966,50).

The starting compounds of Formula II employed in the preparative process of this invention can be produced from 11-methylene-18-methyl-4-estrene-3,17-dione (See, e.g., DOS No. 2,361,120 whose disclosure is incorporated by reference herein) as follows:

15α-Hydroxy-18-methyl-11-methylene-4-estrene-3,17-dione

A 2-liter Erlenmeyer flask containing 500 ml of a nutrient solution of 3.0% glucose, 1.0% cornsteep liquor, 0.2% NaNO$_3$, 0.1% KH$_2$PO$_4$, 0.2% K$_2$HPO$_4$, 0.05% MgSO$_4$.7H$_2$O, 0.002% FeSO$_4$.7H$_2$O, and 0.05% KCl, sterilized for 30 minutes at 120° C. in an autoclave, is inoculated with a slanted tube culture of the strain Penicillium patulum (ATCC 10120) and shaken on a rotary shaker for 2½ days at 30° C.

A 20-liter preliminary fermentor is inoculated with this germination culture; this fermentor is filled with 15 l of a medium having the same composition as the germination culture and sterilized for 60 minutes at 121° C. and 1.1 atm. gauge. With the addition of silicone SH as the defrother, the culture is germinated at 29° C. and a pressure of 0.7 atm. gauge under aeration (15 l/min) and agitation (220 rpm) for 24 hours.

Thereafter 0.9 l of this culture is withdrawn under sterile conditions and used for inoculating a 20-liter main fermentor charged with 14 l of a nutrient medium having the same composition as the preliminary fermentor culture and sterilized as above. After a growth phase of 12 hours under preliminary fermentor conditions, a solution of 4.5 g of 18-methyl-11-methylene-4-estrene-3,17-dione in 100 ml of dimethylformamide is added, and the batch is further stirred and aerated. The progress of fermentation is controlled by taking samples which are extracted with methyl isobutyl ketone and analyzed by thin-layer chromatography. After a contact period of 36 hours, the conversion of the substrate is completed. The culture broth is freed of fungal mycelium by centrifuging in a continuous centrifuge; the clear filtrate is extracted three times with respectively 10 l of methyl isobutyl ketone, and the extracts are combined with the extract of the mycelium, which latter has also been extracted with methyl isobutyl ketone. After concentrating the solution in a forced circulation evaporator, the mixture is then concentrated to dryness at a bath temperature of 50° C. under vacuum in a rotary evaporator. The oily-crystalline residue is chromatographed over a silica gel column for purifying purposes and eluted with a solvent gradient of 7 l methylene chloride-5 l methylene chloride/2 l acetone. Crystallization from acetone yields 3.1 g of 15α-hydroxy-18-methyl-11-methylene-4-estrene-3,17-dione, mp 228° C.

15α-Acetoxy-18-methyl-11-methylene-4-estrene-3,17-dione 2.2 g of 15α-hydroxy-18-methyl-11-methylene-4-estrene-3,17-dione is reacted in 10 ml of pyridine with 2.5 ml of acetic anhydride under argon at room temperature within 2 hours. The solution is introduced into ice/water. The thus-precipitated crude product is vacuum-filtered, dissolved in ethyl acetate, and dried. Chromatography of the crude product on silica gel with 0-20% acetone/hexane yields 1.7 g of 15α-acetoxy-18-methyl-11-methylene-4-estrene-3,17-dione, mp 176.3° C.

15α-Acetoxy-3,3-(2',2'-dimethyltrimethylenedioxy)-18-methyl-11-methylene-5-estren-17-one 5.0 g of 15α-acetoxy-18-methyl-11-methylene-4-estrene-3,17-dione in 50 ml of methylene chloride and 5 ml of triethyl orthoformate is combined at room temperature with 10 g of 2,2-dimethyl-1,3-propanediol and 30 ml of toluenesulfonic acid. After 5 hours, the mixture is diluted with methylene chloride, washed neutral with water, and the crude product is chromatographed on silica gel with 9-12% acetone/hexane, thus obtaining 3.9 g of 15α-acetoxy-3,3-(2',2'-dimethyltrimethylenedioxy)-18-methyl-11-methylene-5-estren-17-one, mp 185.2° C.

3,3-(2',2'-Dimethyltrimethylenedioxy)-18-methyl-11-methylene-5,15-estradien-17-one 3.5 g of 15α-acetoxy-3,3-(2',2'-dimethyltrimethylenedioxy)-18-methyl-11-methylene-5-estren-17-one is stirred in 30 ml of dioxane with 2.5 ml of 1,5-diazabicyclo[5.4.0]-undecene-(5) at room temperature under argon. After 1 hour, the solution is introduced into ice/water. The thus-precipitated product is filtered off, dissolved in ethyl acetate, washed with water, and dried. Chromatography of the crude product on silica gel with 8-10% acetone/hexane yields 2.1 g of 3,3-(2',2'-dimethyltrimethylenedioxy)-18-methyl-11-methylene-5,15-estradien-17-one, mp 184.4° C.

With ethanedithiol/boron trifluoride etherate in place of 2,2-dimethyl-1,3-propanediol/triethyl orthoformate/toluenesulfonic acid, the product is 3,3-ethylenedithio-18-methyl-11-methylene-4,15-estradien-17-one.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a)

17α-Ethinyl-3,3-(2',2'-dimethyltrimethylenedioxy)-18-methyl-11-methylene-5,15-estradien-17β-ol Acetylene is passed for 30 minutes through a solution, cooled with ice/water, of 35 ml of butyllithium (15% in hexane) in 80 ml of absolute tetrahydrofuran (THF). The reaction mixture is combined with 1.0 g of 3,3-(2',2'-dimethyltrimethylenedioxy)-18-methyl-11-methylene-5,15-estradien-17-one in 10 ml of THF are stirred under argon. After 30 minutes, the mixture is combined with saturated ammonium chloride solution, diluted with ethyl acetate, washed with water, and dried. Recrystallization of the crude product from acetone/hexane yields 1.0 g of 17α-ethinyl-3,3-(2',2'-dimethyltrimethylenedioxy)-18-methyl-11-methylene-5,15-estradien-17β-ol, mp 214.1° C.

(b)

17α-Ethinyl-17β-hydroxy-18-methyl-11-methylene-4,15-estradien-3-one 950 mg of 17α-ethinyl-3,3-(2',2'-dimethyltrimethylenedioxy)-18-methyl-11-methylene-5,15-estradien-17β-ol is combined in 20 ml of acetone at room temperature with 0.5 ml of semiconcentrated hydrochloric acid. After 45 minutes, the solution is neutralized with NaHCO₃ solution and exhaustively evaporated under vacuum. The residue is dissolved in ethyl acetate and dried. Recrystallization from acetone/hexane yields 370 mg of 17α-ethinyl-17β-hydroxy-18-methyl-11-methylene-4,15-estradien-3-one, mp 151.2° C.

EXAMPLE 2

(a)

17α-Chloroethinyl-3,3-(2',2'-dimethyltrimethylenedioxy)-18-methyl-11-methylene-5,15-estradien-17β-ol At 0° C. and with introduction of argon, 12 ml of a 5% ethereal methyllithium solution is added dropwise to 1.6 ml of 1,2-dichloroethylene in 10 ml of absolute ether. After 30 minutes, 700 mg of 3,3-(2',2'-dimethyltrimethylenedioxy)-18-methyl-11-methylene-5,15-estradien-17-one in a mixture of 15 ml of ether and 5 ml of THF is added to the reaction mixture and the latter is agitated at room temperature. After 15 minutes, the mixture is gently combined with saturated ammonium chloride solution, diluted with ether, washed with water, and dried. Recrystallization of the crude product from acetone/hexane yields 650 mg of 17α-chloroethinyl-3,3-(2',2'-dimethyltrimethylenedioxy)-18-methyl-11-methylene-5,15-estradien-17β-ol, mp 186.6° C.

(b)

17α-Chloroethinyl-17β-hydroxy-18-methyl-11-methylene-4,15-estradien-3-one 600 mg of 17α-chloroethinyl-3,3-(2',2'-dimethyltrimethylenedioxy)-18-methyl-11-methylene-5,15-estradien-17β-ol in 20 ml of acetone is stirred at room temperature under argon with 0.5 ml of semiconcentrated hydrochloric acid. After 1½ hours, the mixture is neutralized with NaHCO₃ solution and extensively concentrated under vacuum. The residue is dissolved in ethyl acetate, washed with water, and dried. Recrystallization of the crude product from acetone/hexane yields 317 mg of 17α-chloroethinyl-17β-hydroxy-18-methyl-11-methylene-4,15-estradien-3-one, mp 149° C.

EXAMPLE 3

(a)

3,3-(2',2'-Dimethyltrimethylenedioxy)-18-methyl-11-methylene-17α-(1-propinyl)-5,15-estradien-17β-ol Methylacetylene is conducted for 30 minutes through a solution, cooled with ice/water, of 40 ml of butyllithium (15% in hexane) in 100 ml of absolute THF. The mixture is combined with 2.4 g of 3,3-(2',2'-dimethyltrimethylenedioxy)-18-methyl-11-methylene-5,15-estradien-17-one in 10 ml of THF and stirred under argon at room temperature. After 2 hours, saturated ammonium chloride solution is added dropwise to the reaction solution; the latter is diluted with ethyl acetate, washed with water, and dried. After chromatography of the crude product with 0–15% acetone/hexane on silica gel, 2.1 g of 3,3-(2',2'-dimethyltrimethylenedioxy)-18-methyl-11-methylene-17α-(1-propinyl)-5,15-estradien-17β-ol is obtained as a foamy product.

(b)

17β-Hydroxy-18-methyl-11-methylene-17α-(1-propinyl)-4,15-estradien-3-one

At room temperature, 0.2 ml of semiconcentrated hydrochloric acid is added to 520 mg of 3,3-(2',2'-dimethyltrimethylenedioxy)-18-methyl-11-methylene-17α-(1-propinyl)-5,15-estradien-17β-ol in 10 ml of acetone. After 30 minutes, the solution is neutralized with saturated NaHCO₃ solution and exhaustively concentrated under vacuum. The residue is dissolved in ethyl acetate, washed with water, and dried. The crude product is purified by preparative layer chromatography (eluent: ether/chloroform 8:2), thus obtaining 170 mg of 17β-hydroxy-18-methyl-11-methylene-17α-(1-propinyl)-4,15-estradien-3-one.

EXAMPLE 4

17β-Acetoxy-17α-ethinyl-18-methyl-11-methylene-4,15-estradien-3-one 1.2 g of 17α-ethinyl-17β-hydroxy-18-methyl-11-methylene-4,15-estradien-3-one in 10 ml of pyridine is reacted at room temperature with the addition of 100 mg of 4-dimethylaminopyridine with 6.5 ml of acetic anhydride. The mixture is introduced into ice/water after 5 hours. The thus-precipitated product is vacuum-filtered, dissolved in ethyl acetate, and washed with water. Chromatography of the crude product on silica gel with acetone/hexane yields 710 mg of 17β-acetoxy-17α-ethinyl-18-methyl-11-methylene-4,15-estradien-3-one as a frothy product.

EXAMPLE 5

17β-butyryloxy-17α-ethinyl-18-methyl-11-methylene-4,15-estradien-3-one 500 mg of 17α-ethinyl-17β-hydroxy-18-methyl-11-methylene-4,15-estradien-3-one in 6 ml of pyridine is stirred at room temperature with 2.5 ml of butyric anhydride and 120 mg of 4-dimethylaminopyridine. After 4 hours, the mixture is introduced into ice/water, extracted with methylene chloride, and washed with water. Chromatography of the crude product on silica gel with acetone/hexane yields 320 mg of 17β-butyryloxy-17α-ethinyl-18-methyl-11-methylene-4,15-estradien-3-one as an oil.

EXAMPLE 6

17α-Ethinyl-17β-heptanoyloxy-18-methyl-11-methylene-4,15-estradien-3-one 250 mg of 17α-ethinyl-17β-hydroxy-18-methyl-11-methylene-4,15-estradien-3-one in 4 ml of pyridine is stirred at room temperature with 2 ml of enanthic anhydride and 60 mg of 4-dimethylaminopyridine for 20 hours. The mixture is introduced into ice/water, extracted with methylene chloride, and the solution washed with water. After chromatography of the crude product on silica gel with acetone/hexane, 110 mg of 17α-ethinyl-17β-heptanoyloxy-18-methyl-11-methylene-4,15-estradien-3-one is obtained in the form of an oil.

EXAMPLE 7

17β-Acetoxy-17α-chloroethinyl-18-methyl-11-methylene-4,15-estradien-3-one 350 mg of 17α-chloroethinyl-17β-hydroxy-18-methyl-11-methylene-4,15-estradien-3-one in 5 ml of pyridine is reacted at room temperature with 2 ml of acetic anhydride and 20 ml of 4-dimethylaminopyridine. After 3 hours, the solution is poured into ice/water. The thus-precipitated product is vacuum-filtered, dissolved in methylene chloride, and washed with water. Chromatography of the crude product on silica gel with acetone/hexane yields 180 mg of 17β-acetoxy-17α-chloroethinyl-18-methyl-11-methylene-4,15-estradien-3-one as a frothy product.

EXAMPLE 8

17β-Butyryloxy-18-methyl-11-methylene-17α-(1-propinyl)-4,15-estradien-3-one 230 mg of 17β-hydroxy-18-methyl-11-methylene-17α-(1-propinyl)-4,15-estradien-3-one in 3.5 ml of pyridine is agitated at room temperature with 2.0 ml of butyric anhydride and 100 mg of 4-dimethylaminopyridine. After 10 hours, the solution is introduced into ice-water, extracted with methylene chloride, washed with water, and the crude product chromatographed on silica gel with acetone/hexane, thus isolating 85 mg of 17β-butyryloxy-18-methyl-11-methylene-17α-(1-propinyl)-4,15-estradien-3-one as an oil.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11-Methylene-Δ¹⁵-steroid of the formula

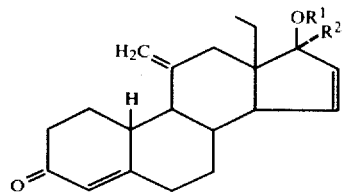

wherein
R¹ is hydrogen or an acyl group of a $C_{1-15}$ hydrocarbon carboxylic acid, and
R² is ethynyl, chloroethynyl or propynyl.

2. 17α-Ethynyl-17β-hydroxy-18-methyl-11-methylene-4,15-estradien-3-one, a compound of claim 1.

3. 17α-Chloroethynyl-17β-hydroxy-18-methyl-11-methylene-4,15-estradien-3-one, a compound of claim 1.

4. 17β-Hydroxy-18-methyl-11-methylene-17α-(1-propynyl)-4,15-estradien-3-one, a compound of claim 1.

5. 17β-Acetoxy-17α-ethynyl-18-methyl-11-methylene-4,15-estradien-3-one, a compound of claim 1.

6. 17β-Butyryloxy-17α-ethynyl-18-methyl-11-methylene-4,15-estradien-3-one, a compound of claim 1.

7. 17α-Ethynyl-17β-heptanoyloxy-18-methyl-11-methylene-4,15-estradien-3-one, a compound of claim 1.

8. 17β-Acetoxy-17α-chloroethynyl-18-methyl-11-methylene-4,15-estradien-3-one, a compound of claim 1.

9. 17β-Butyryloxy-18-methyl-11-methylene-17α-(1-propynyl)-4,15-estradien-3-one, a compound of claim 1.

10. A compound of claim 1 wherein R¹ is H or $C_{1-7}$-alkanoyl.

11. A pharmaceutical composition comprising a progestationally effective amount of a compound of claim 1 and a pharmaceutically acceptable adjuvant.

12. A pharmaceutical composition of claim 11 further comprising an estrogenically effective amount of an estrogen.

13. A method of achieving a progestational effect in a patient in need of such treatment comprising administering to the patient a progestationally effective amount of a compound of claim 1.

14. A method of claim 13 wherein the effect is inhibition of ovulation and there is also administered to the patient an estrogenically effective amount of an estrogen.

* * * * *